United States Patent [19]

Crandall et al.

[11] Patent Number: 4,922,925
[45] Date of Patent: May 8, 1990

[54] COMPUTER BASED UPPER EXTREMITY EVALUATION SYSTEM

[75] Inventors: Richard E. Crandall; Paul M. Weeks, both of St. Louis, Mo.; Michael W. Vannier, Edwardsville, Ill.

[73] Assignee: Washington University, St. Louis, Mo.

[21] Appl. No.: 314,188

[22] Filed: Feb. 27, 1989

Related U.S. Application Data

[63] Continuation of Ser. No. 162,263, Feb. 29, 1988, abandoned.

[51] Int. Cl.⁵ .............................................. A61B 5/10
[52] U.S. Cl. ..................................................... 128/782
[58] Field of Search ............... 128/774, 779, 781, 782; 307/147; 33/511, 512, 515

[56] References Cited

U.S. PATENT DOCUMENTS

| | | | |
|---|---|---|---|
| T100,602 | 5/1981 | Roley et al. | 128/782 |
| 3,822,694 | 7/1974 | Mills | 128/653 |
| 3,868,565 | 2/1975 | Kuipers | 324/34 R |
| 3,983,474 | 9/1976 | Kuipers | 324/43 R |
| 4,017,858 | 4/1977 | Kuipers | 343/100 R |
| 4,054,881 | 10/1977 | Raab | 343/112 R |
| 4,108,164 | 8/1978 | Hall, Sr. | 128/781 |
| 4,197,855 | 4/1980 | Lewin | 128/653 |
| 4,298,874 | 11/1981 | Kuipers | 343/112 R |
| 4,306,571 | 12/1981 | McLeod, Jr. | 128/782 |
| 4,314,251 | 2/1982 | Raab | 343/112 R |
| 4,328,548 | 5/1982 | Crow et al. | 364/449 |
| 4,337,050 | 6/1982 | Engalitcheff, Jr. | 434/260 |
| 4,346,384 | 8/1982 | Raab | 343/112 R |
| 4,355,645 | 10/1982 | Mitani et al. | 128/777 |
| 4,371,836 | 2/1983 | Nickel et al. | 324/207 |
| 4,383,535 | 5/1983 | Schorr | 128/777 |
| 4,386,405 | 5/1983 | Lewin et al. | 364/415 |
| 4,436,099 | 3/1984 | Raftopoulos | 128/782 |
| 4,444,205 | 4/1984 | Jackson | 128/774 |
| 4,447,207 | 5/1984 | Kataoka et al. | 433/69 |
| 4,461,085 | 7/1984 | Dewar et al. | 33/174 L |
| 4,495,952 | 1/1985 | Klett | 128/777 |
| 4,530,367 | 7/1985 | Desjardins et al. | 128/777 |
| 4,534,364 | 8/1985 | Lamoreux | 128/774 |
| 4,542,291 | 9/1985 | Zimmerman | 250/231 R |
| 4,549,555 | 10/1985 | Fraser et al. | 128/782 |
| 4,571,834 | 2/1986 | Fraser et al. | 128/782 |
| 4,608,998 | 9/1986 | Murdock | 128/782 |
| 4,631,477 | 12/1986 | Nickel et al. | 324/207 |
| 4,642,480 | 2/1987 | Hughes et al. | 307/147 |
| 4,649,934 | 5/1987 | Fraser et al. | 128/774 |
| 4,655,227 | 4/1987 | Gracovetsky | 128/781 |
| 4,667,685 | 5/1987 | Fine | 128/782 |
| 4,699,156 | 10/1987 | Gracovetsky | 128/781 |
| 4,760,851 | 8/1988 | Fraser et al. | 128/774 |

FOREIGN PATENT DOCUMENTS 8702567  5/1987  World Int. Prop. O. .......... 128/782

OTHER PUBLICATIONS

Article from Oct. 1987 Issue of *Scientific American* entitled "Interfaces for Advanced Computing".
Publication for RESNA 10th Annual Conference in 1987 entitled "Initial Experience with the Data Glove, a Semi-Automated System for Quantification of Hand Function".
1986 Proceedings of SPIE *Intelligent Robots and Computer Vision* entitled "Telepresence master glove controller for dexterous robotic end-effectors".
"Kinematic Analysis of Human Wrist Motion Using a Six-Degree of Freedom Digitizer and Computer Assisted Design System" by Logan, Vannier, Bresina, and Weeks published from American College of Surgeons 1985 Surgical Forum Volume XXXVI.

(List continued on next page.)

*Primary Examiner*—Max Hindenburg
*Attorney, Agent, or Firm*—Rogers, Howell & Haferkamp

[57] ABSTRACT

An upper extremity evaluation system includes a computer and a directly connected three-dimensional position locator which may be used by a therapist to enter data corresponding to the location of the flexed and extended joints of the hand, wrist and elbow. The computer may then utilize these dimensions in calculating angles of flexion and extension, and a degree of disability in accordance with American Medical Association standards.

15 Claims, 1 Drawing Sheet

OTHER PUBLICATIONS

*Progress in Biomechanics* published in 1979, including a chapter "Biomechanical Aspects of Plastic Surgery" by Prof. Tom Gibson.

Proceedings of the Seventh N.E. Bioengineering Conference, L. L. Ostrander, Editor, 1979 "Error and Optimization Study of the Instantaneous Center and Angle of Rotation of a Body Joint" by Manohar Panjabi.

August 1982 Transactions of the ASME article entitled "Errors in the Center and Angle of Rotation of a Joint: an Experimental Study" by Panjabi, Goel, Walter and Schick.

ASME 1982 Advances in Bioengineering article entitled "Screw Axis Measurement in the Human Wrist".

IEEE Transactions on Aerospace and Electronic Systems in September 1979 article entitled "Magnetic Position and Orientation Tracking System".

SAE Technical Paper Series 1983 article entitled "Three-Dimensional Digitization of Real World Objects" by J. T. Scully.

*Journal of Biomechanics* 1981 article entitled "A Techique for Measurement and Description of Three-Dimensional Six Degree-of-Freedom Motion of a Body Joint with an Application to the Human Spine" by Panjabi, Krag, and Goel.

Proceedings of the European Society of Biomechanics 1984 article entitled "Biomechanics: Current Interdisciplinary Research".

Abstract published in 1986 entitled "Carpal Bone Motion Axes and Pivots in Flexion and Deviation of the Hand".

Abstract published in 1984 entitled "Minimum Variance Estimation of Continuous, 2-D and 3-D Rigid Body Movement from Noisy Measurements on Bandwidth-Limited Landmark Position Data".

Reprint from the Magazine *Human Movement Science*, 1985 entitled "On Optimal Smoothing and Derivative Estimation from Noisey Displacement Data in Biomechanics".

1982 article entitled "Analysis and Display of Human Wrist Motion" by Peterson and Erdman.

*Advances in Engineering Software* article published in 1986 entitled "A Fortran Package Generalized Cross--Validatory Spline Smoothing and Differentiation".

Article published in 1976 entitled "The Ligaments of the Human Wrist and Their Functional Significance".

Abstract from the Symposium on Biodynamic Models and Their Applications in 1970 entitled "Control of the Human Forearm During Abrupt Acceleration".

*Journal of Bioengineering* 1977 article entitled "Laboratory Reproduction in In-Vivo Loads in a Biological Structure".

*The Journal of Hand Surgery* 1985 article entitled "Functional Wrist Motion: A Biomechanical Study".

Article printed in 1979 entitled "A Biomechanical Investigation of Wrist Kinematics".

*Journal of Biomechanical Engineering* 1980 article entitled "A Technique for Kinematic Modeling of Anatomical Joints".

Transactions of the ASME 1982 article entitled "An In—Vivo Study of Normal Wrist Kinematics".

Transactions of the ASME 1979 article entitled "Kinematic and Kinetic Analysis of the Human Wrist by Stereoscopic Instrumentation".

*Journal of Bioengineering*, 1978 article entitled "Instantaneous Center of Rotation by Least Square Method".

*Journal of Bioengineering*, 1978 article entitled "An Accurate Data Collection Method for Spatial Motion Using a Sonic Digitizer".

*Medical and Biological Engineering and Computing*, May 1981 article entitled "Kinematic Data Acquisition System for Two- or Three- Dimensional Motion Analysis".

1979 article entitled "Biomechanical Analyses of Forearm Pronation—Supination and Elbow Flexion-Extension".

1978 article entitled "Methods, Difficulties and Inaccuracies in the Study of Human Joint Kinematics and Pathokinematic by the Instant Axis Concept, Example: The Knee Joint".

Transactions of the ASME, May 1979 article entitled "Kinematic and Kinetic Analysis of the Human Wrist by Stereoscopic Instrumentation".

Publication from 1987 Advances in Bioengineering ASME, article entitled "Elbow Kinematic Study by Using 3Space TM Isotrak TM ".

Orthopedic Clinics of North America Jul. 1986 publication, article entitled "Scaphoid Orientation and Location from Computed, Three-Dimensional Carpal Models".

*Journal of Biomechanics* 1985 article entitled "The Kinematics of Normal and Prosthetic Wrists".

(List continued on next page.)

OTHER PUBLICATIONS

*Journal of Biomechanics* 1976 article entitled "A Technique for Joint Center Using a Stored Program Calculator".

1982 Transactions of the IEEE article entitled "Effects of Measurement Errors in Describing Human Joint Motion".

*Journal of Biomechanics* 1980, a Technical Note entitled "Rigid Body Motion Calculated From Spatial Co-ordinates of Markers".

*Journal of Orthopaedic Research* 1985 article entitled "Kinematic Behavior of the Human Wrist Joint: A Roentgen-Stereophotogrammetric Analysis".

*The Journal of Hand Surgery* Jan. 1985 article entitled "Three-Dimensional Imaging of the Wrist".

Proceedings of the Physiological Society, 1974 abstract entitled "A torque-induced motion analyser".

Clinics in Rheumatic Diseases 1982 article entitled "The Wrist".

Paper presented at Annual Meeting of the American Society for Surgery of the Hand in 1971 entitled "Traumatic Instability of the Wrist".

American Society for Surgery of the Hand 1981 article entitled "The triangular fibrocartilage complex of the wrist—Anatomy and function".

*Journal of Hand Surgery* 1983 article entitled "Instability patterns of the wrist".

*American Journal of Physical Science* 1971 article entitled "Kinesiology of the Wrist".

Clinical Orthopaedics and Related Research 1980 article entitled "Kinematics of the Wrist".

Clinical Orthopaedics and Related Research 1980 article entitled "Biomechanisms of the Wrist".

Article published in 1979 entitled "Analytical Development in Investigation of Wrist Kinematics

*Journal of Hand Surgery* 1976 article entitled "The pronator quadratus in motions and in stabilization of the radius and ulna at the distal radioulnar joint".

*Journal of Neuroscience* 1982 article entitled "Coordination of Arm and Wrist Motion During a Reaching Task".

*Journal of Biomechanics* 1979 article entitled "Some Biomechanical Aspects of the Carpal Tunnel".

Article published in 1976 entitled "The Ligaments of the Human Wrist and Their Functional Significance".

*Arch Phys Med Rehabil* 1973 article entitled "Effects of Immobilization in the Human Forearm".

*Brain Research* 1981 article entitled "Correlation of monkey pyramidal tract neuron activity to movement velocity in rapid wrist flexion movement".

*Clinical Orthopaedics and Related Research* 1980 article entitled "Functional Anatomy of the Wrist".

*Clinical Orthopaedics and Related Research* 1980 article entitled "Mechanism of Carpal Injuries".

*Clinical Orthopaedics and Related Research* 1980 article entitled "Arthroplasty of the Wrist".

*Journal of Bone and Joint Surgery* 1982 article entitled "Correction of Post-Traumatic Wrist Deformity in Adults by Osteotomy, Bone-Grafting, and Internal Fixation".

Article entitled "Wrist Kinematic Analysis Using A 6 Degree of Freedom Digitizer" published in *Proceedings of the Seventh Annual Conference of the IEEE Engineering in Medicine and Biology Society, Sep. 1985.*

Advertising brochure of Polhemus Navigation Sciences Division of McDonnell Douglas Electronics Company, dated Dec. 1, 1983 for the 3Space Three-Dimensional Digitizer.

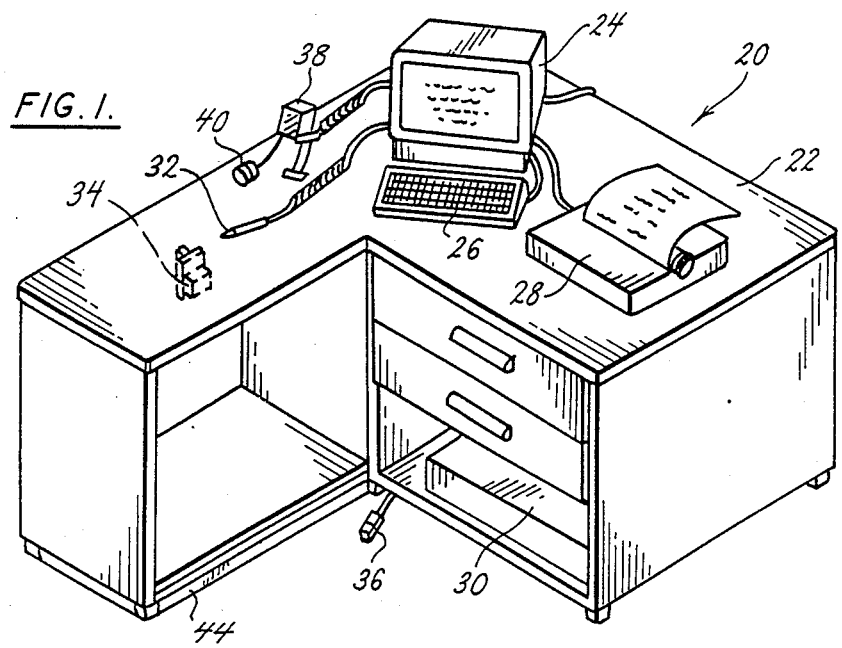
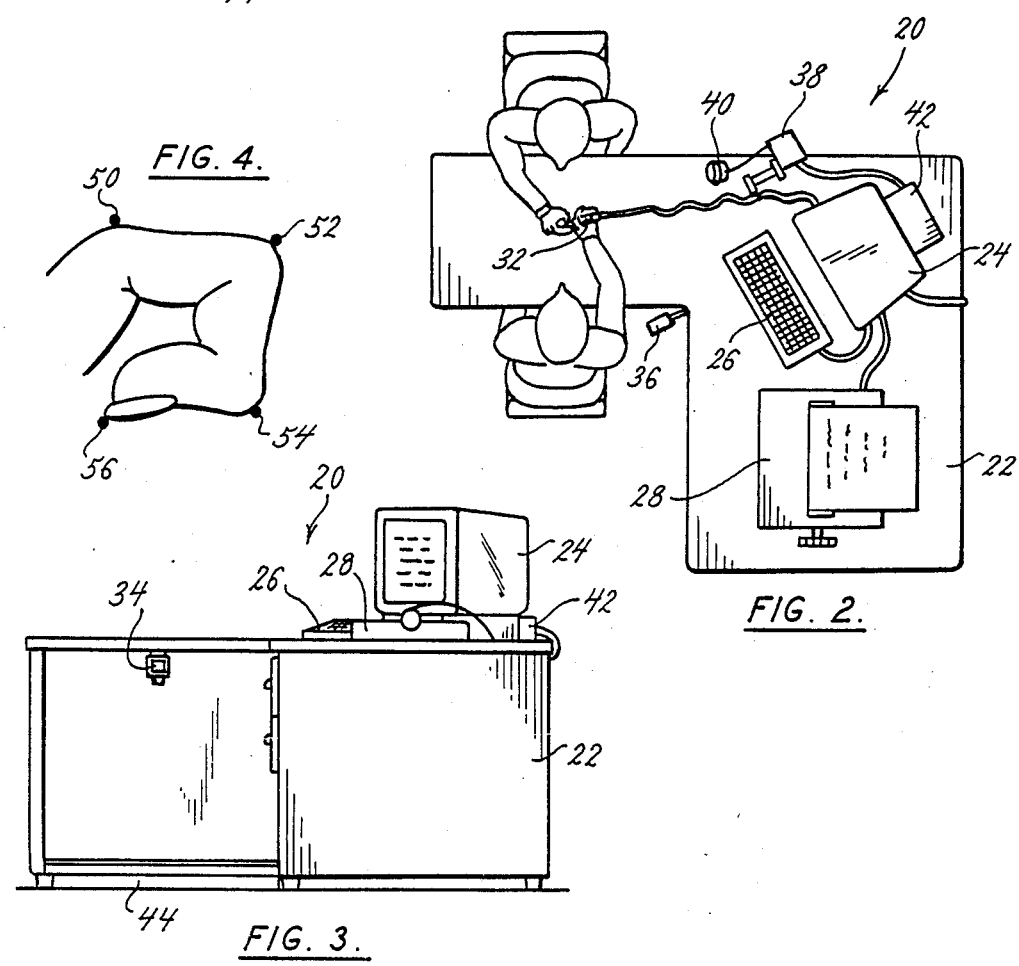

COMPUTER BASED UPPER EXTREMITY EVALUATION SYSTEM

This is a continuation of copending application Ser. No. 07/162,263; filed on Feb. 29, 1988, now abandoned.

BACKGROUND AND SUMMARY OF THE INVENTION

Clinical evaluation of a patient's upper extremities, and more particularly the hands, for disability can be a time-consuming process for skilled therapists and physicians. Because of the unique complexity of the hands' movements, multiple measurements must be taken across all joints of the fingers to determine their maximum angle of flexion and extension. There are fourteen joints or knuckles in a normal hand, and each of these must be measured in flexion and extension to arrive at a measure of the disability of the hand as is often required for proper clinical evaluation and for the patient to obtain compensation for an injury which has limited his range of motion. At present, a therapist must sit with a patient and manually measure each individual angle of flexion and extension for each joint with a goniometer by isolating the joint, aligning it with the legs of the goniometer, and manually recording the measured included angle. Not only is this process tedious and time-consuming, and thus expensive to perform, but less time remains for the therapist to perform physical therapy with the patient. During the course of a patient's treatment, it is desirable to repeat these measurements over the time course of therapy to assess a patient's progress. Unfortunately, because there is some subjective element in the use of the goniometer and the current standard technique used in making hand function measurements, the repeatability of any particular examination is relatively poor. The variance of measurements from therapist to therapist has been so large with the standard goniometer so that the same therapist should measure the same patients each evaluation session. This is often not possible in a busy therapy center. This leads to uncertainty and ineffectiveness in assessing the patient's functional status and in designing treatment protocols.

Some attention has been paid in the prior art to the problem of evaluating and measuring the range of motion in the knee. Examples of these are found in U.S. Pat. Nos. 4,549,555 and 4,571,834. These references both contain the same disclosure relating to a knee laxity evaluator comprised of an instrumented seat, a restraint for restraining the thigh of the patient to the instrumented seat, a motion module consisting of a mechanical coupling extending between the seat and the patient's leg with a number of electromechanical rotary transducers for measuring the relative position of the leg, and a processor for analyzing the outputs of the seat and the motion modules to provide an indication of applied force and relative motion of the knee. The device disclosed is mechanically and operationally complex and is limited in its accuracy although it is probably adequate as measuring knee motion of a knee joint which is a very large joint whereas measuring finger motion requires much more delicate instrumentation.

Perhaps because of the bulky, mechanically complex construction of the device disclosed in these prior patents, the inventors herein are aware of a later commercial model of this device which is adapted for use with the spine which is comprised of a wand mounted at the end of a multi-jointed mechanical arm, the arm being adjustably mounted to a pole stand and having a rotary transducer at each of the joints of the arm. Apparently, a foot switch is also provided and the device is understood to be used by tracing an exterior outline corresponding to the perceived position of posterior elements and spinous processes in the spine with the wand as the foot switch is operated to input data corresponding to the shape of the spine to a computer which then performs an analysis including flexibilty and range of motion measurement. However, as with the prior art device disclosed in the patents mentioned above, the overall accuracy is limited by the use of the three rotary mono-angular (mono-articulated) single DOF transducers in the multi-jointed extension arm which are believed to generate only relative position data obtained by integrating a plurality of measurements over time, although the level of accuracy attainable is probably more than adequate for the measurement of the posterior elements of the dossal and lumbar spine.

The inventors herein are also aware of a prior art device consisting of a "data glove" as is described generally in U.S. Pat. No. 4,542,291 and also in a *Scientific American* magazine article appearing on the cover and within the October 1987 issue. This device is essentially comprised of a glove which is slipped onto and encloses the hand and which contains a plurality of fiber-optic cables anchored at both ends to an interface board which run the length of each finger and doubles back. As the hand is measured, it is not visible to the operator. Each cable has a light-emitting diode at one end and a phototransistor at the other with the cables being treated so that light escapes when a finger flexes. Thus, a change in the amount of light received by the phototransistor, when converted into an electrical signal, is directly representative of a change in position or flexion of the finger such that the data glove can measure relative movement of the finger as it is flexed or extended. Additionally, an absolute position and orientation sensor is mounted near the wrist of the glove to provide a single absolute point of reference for the entire hand, although it does not provide data as to the position or angle of flexion or extension of any of the fingers themselves. The data glove provides simultaneous real time measurements concerning the relative motion or movement of the fingers but does not provide data corresponding to the absolute position of any of the fingers. Thus, to measure an angle of maximum flexion at each joint, the finger must first be placed in a known position and then the finger flexed to its position of maximum flexion as the output of the data glove is continuously monitored. The maximum angle of flexion may then be determined by comparing this known starting position with the angle of flexion computed by integrating continuously recorded measurements. of course, there is some uncertainty in determining and repeating a known initial position and angle for a finger before it is flexed, especially if that finger is incapable of a full and complete range of motion. Once again, as with the prior art manual technique, and the rotary transducers of the prior art knee de vice, significant potential for error and subjectivity enter into the measurement of angles of flexion and extension with the data glove. There is no provision for competent human intervention in the operation of the data glove.

Still another problem in evaluating the hand is the complex nature of the wrist. Presently, in accepted standards of medical practice, the range of motion for the wrist is determined by having the patient grip a cylindrical object such as a pencil or the like, and holding the pencil in a vertical orientation which is defined as a neutral position. The patient is then told to rotate the pencil inwardly to its maximum extent and the angle is measured, and then to rotate the pencil outwardly to its maximum extent and that angle is measured as well. These angular measurements can then be used to determine the maximum pronation and supination. However, it is known that there is approximately 30° of additional total rotation contained in the joints between the radius and ulna and the fingers such that these measurements are not the true measurements of the range of motion of the wrist. Thus, there exists no protocol or methodology in the prior art to properly fully evaluate the true range of motion of the wrist. Furthermore, none of the prior art devices discussed above are capable of generating data which accurately provides the range of motion for the wrist. This is partially due to the fact that it is difficult to visualize the radius and ulna as the wrist is rotated, and for the further reason that the prior art systems have errors of measurement which are significant in measuring the small distances which through the wrist rotates.

To solve these and other problems in the prior art, the inventors herein have succeeded in designing and developing an upper extremity evaluation system which is particularly adapted to and useful in measuring the range of flexion and extension of the joints of the hand, wrist and elbow and automatically calculating a degree of disability in accordance with American Medical Association (AMA) standards commonly used by the courts and workers compensation boards in determining the financial compensation due to a patient for an injury. In a distinct departure from the prior art, the inventors have succeeded in adapting a three-dimensional spatial absolute position and orientation sensor into a computer measurement system which permits the convenient collection of data by a therapist corresponding to the absolute position of the proximal and distal segments at a joint in the fully extended as well as the fully flexed position. In other words, a therapist can quickly and conveniently enter data automatically into the computer which corresponds to the position of the various joints of the patient's hand as the hand is manipulated into one of only several different positions and held for only a brief period of time therein. Because absolute position data is measured and collected, much greater accuracy is attainable. Furthermore, because of the convenient methodology used to collect the data, an evaluation is also capable of a high level of repeatability. This has a dramatic impact on the accuracy of the initial assessment given to a patient, as well as the evaluation of treatment protocols through the course of the patient's rehabilitation. Still another advantage with the inventors' system is that for the first time accurate range of motion information can be easily collected by measuring the exact location of the radial and ulna styloid processes while the wrist is held in the neutral, supinated, and pronated positions. The computer may then eliminate the translation of these bones as they are moved from the computation to arrive at a true and accurate measure of the wrist's range of motion. Further information may also be obtained relating to the range of supination and pronation at the metacarpal level, which provide additional functional information of interest to the surgeon. However, perhaps the greatest advantage of the device is that it dramatically reduces the amount of therapists' time required to perform the clinical evaluation, and virtually eliminates the hand surgeon's time in evaluating the therapists' results. This is all achieved while significantly increasing the reliability and variability of the results.

In addition to measuring the angles of maximum flexion and extension, a dynamometer and pinch gauge are also connected directly to the computer for the direct entry of data corresponding to the grip strength and pinching strength of the hand and fingers. Still further data may be taken corresponding to other measurements, such as sensitivity, through the keyboard provided with the computer. Thus, the upper extremity evaluation system of the present invention permits a therapist to make an evaluation of any of the upper extremities, to input data gained through subjective manual measurements, and to permit such desired manipulation and calculation of the data to arrive at a degree of disability in accordance with AMA standards.

Briefly, the protocol for entering data corresponding to the hand includes locating twenty-four specific points on the dorsal surface of the hand in a sequence which permits the most rapid data collection as well as to give maximum flexion values. This begins with the four points on the fully flexed thumb, taken in a proximal to distal fashion, thus measuring the metacarpal phalangeal (MP) and interphalangeal (IP) joints. Then, with the fingers maximally flexed in a fist and the thumb abducted, the first four points on the remaining digits are digitized, again proximal to distal, one digit at a time, beginning with the index finger and moving ulnarly. These four points correspond to a mid-thumb metacarpal, MP apex, IP apex, and thumb nail for the thumb. For each digit, five points correspond to the midmetacarpal, MP apex, proximal interphalangeal (PIP) apex, distal interphalangeal (DIP) apex, and fingernail. The first four points are digitized. This measures the MP and PIP joints. For the DIP joint, the fingers are extended at the MP joints and flexed at the PIP and DIP joints. Using the same digit order, the third, fourth and fifth points are redigitized. As can be appreciated, this protocol can be routinely performed by an average therapist in less than two minutes. Data entry is achieved by touching the finger or hand with a wand or pointer, and pressing a foot switch when the wand or pointer is in the appropriate and desired location. This permits the therapist to choose the point in time for data entry to provide greater control over the evaluation.

A software package which operates on the control desktop personal microcomputer has been designed and developed by the inventors which guides and instructs the therapist as he/she proceeds through the evaluation process. This ensures a complete examination taken with the same methodology and helps improve the accuracy of results. In the prior art, significant inconsistencies of results are often noticed between therapists examining the same patient. With the present invention, these inconsistencies are thought to be significantly reduced. Furthermore, the software calculates angles of flexion and extension from the position data entered by the therapist and makes further calculations in accordance with AMA standards to arrive at the degree of disability. A hand surgeon may then review these results and verify them in accordance with accepted medical practice. However, because of the increased reliability brought to the measurement and data entry portions of the evaluation, the amount of time and involvement of the hand surgeon can be significantly reduced thereby significantly reducing the cost of the evaluation to the patient while improving the results obtained thereby.

While the principal advantages and features of the present invention have been briefly described, a fuller understanding may be attained by referring to the drawings and description of the preferred embodiment which follow.

BRIEF DESCRIPTION OF THE DRAWINGS

FIG. 1 is a perspective view of a work station including the computer, printer, three-dimensional locator, and peripherals;

FIG. 2 is a top view of the work station of FIG. 1 with a patient and therapist depicted in a typical examination of an upper extremity (hand);

FIG. 3 is a side view of the work station of FIG. 1 detailing the mounting of the reference point for the three-dimensional point locator; and FIG. 4 is a side view of a finger with joints flexed into maximum flexion with points of measurement indicated thereon.

DETAILED DESCRIPTION OF THE PREFERRED EMBODIMENT

The upper extremity evaluation system 20 of the present invention can be conveniently mounted in a work station 22 wherein a small personal computer 24 such as a Macintosh SE computer (Apple Computer Corporation) with keyboard 26 and mouse may be installed. Additionally, a printer 28 or any other suitable peripheral output device may be utilized to permit automatic preparation of reports and the like as will be further explained herein. A three-dimensional position locator 30 may be interfaced to computer 24 and include a wand or pointer 32 along with a reference sensor 34 and foot switch 36 to permit a therapist to selectively input data to the computer 24 corresponding to the position of a point with respect to sensor 34. A three-dimensional position locator suitable for use herein is the 3SPACE tracker manufactured and sold by Polhemus Navigation Sciences Division of McDonnell Douglas Electronics Company, Colchester, Vermont. Additionally, a grip dynamometer 38 and a pinch gauge 40 may be connected through an interface 42 directly to the computer 24. Examples of typical devices used by the inventors herein include a catalog number 1113 Jamar grip meter and pinch gauge and a MacAdious II SE expansion system interface. The analog signal of the grip meter is converted to a digital signal which is then fed into the computer database through the interface system. To improve the accuracy of the three-dimensional position locator 30, an aluminum panel 44 is mounted along the floor of the work station 22 such that it is thirty inches below the top surface of work station 22, with the reference sensor 34 being mounted five inches below the top surface of the work station 22. It has been found with this arrangement that an improved accuracy can be achieved with the particular components incorporated by the inventors in the best mode of their invention.

To more fully explain the operation of the invention, a sample scenario is contained in Exhibit A attached hereto and incorporated herein. This sample scenario describes the steps required to complete an examination of the upper extremities. The software program which controls the data input and calculation is described in a flow chart with notes attached hereto and incorporated herein as Exhibit B. Although these exhibits are detailed explanations of the system of the present invention, the system may be more briefly described for convenience as follows.

Essentially, the invention provides for the collection of position data of joints placed in flexion and extension which are then used by the computer to calculate angles of flexion and extension. Additionally, the computer provides for prompting of the therapist to enter other related data such as grip data, pinch strength data, sensitivity data, and other typical measurements as is known in the art. Data acquisition is achieved through the software program of Exhibit B. The database software used to create the reports is a standard database software, such as FileMakerPlus as is marketed by Forethought for the Apple Macintosh computer.

Joint range of motion information is collected in a process which combines the three-dimensional position locator and the computer. The therapist must first specify the portions of the upper extremities that will be analyzed, and then designate any joints that are either amputated or fused, the computer assuming that any non-designated joints are normal. The therapist is then prompted to supply the appropriate data through the usage of the present invention. That includes the process of touching the wand 32 to a point such as the MP apex 50 in FIG. 4 and then pressing foot switch 36 to cause entry of the data into the computer. This process is repeated at each of the points PIP apex 52, DIP apex 54, and fingernail 56. The three-dimensional position locator generates digital data corresponding to the relative position of those points 50–56 with respect to the reference sensor 34. From these several points taken about each of the fingers, angles of flexion and extension for those joints may be calculated by the computer. When done quickly by the therapist, there is virtually no tendency for the hands of the patient to be moved and hence the frame of reference is not altered or intended to be altered during the measurement process. After the position information is used to calculate range of motion information, that data is stored in an associated logical record in the computerized database file which can then automatically generate reports In addition to usage of the wand or pointer 32, grip and pinch strength information can be input to the computer through use of the dynamometer 38 and pinch gauge 40. This digital data is stored in a file, similar to the range of motion data file, and is available to the database software to produce reports.

The therapist generally follows the instructions displayed on the screen of the computer to automatically enter range of motion data and grip and pinch strength data to any of the reports. There are three separate reports or forms. These include a data collection form, a final evaluation form, and a second version of the final evaluation form. Of course, any additional forms of any other desired nature may also be produced through simple reprogramming of the database as would be well known to one of ordinary skill in the art. These completed forms may then be printed out on the printer at the request of the therapist.

There are various changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. A clinical range of motion and disability evaluation device for measuring the range of flexion and extension of a patient's hand comprising a computer means, means directly connected to the computer means for a skilled human operator such as a rehabilitative or physical therapist or physician to selectively measure and input various physical locations of the articulated segments which comprise the fingers of the hand, a common reference point, the measuring and input means including means to locate points proximate the various joints of fingers on the hand with respect to said common reference point in a fully three-dimensional Cartesian coordinate form, said measurements being taken with the fingers of the hand in both a flexed and extended orienation, and the computer means having means to determine the degree of disability from said measured locations according to recognized standard criteria, the disability determining means thereby having means to calculate the angles of maximum flexion and extension for each finger from points that locate the absolute position of maximal and distal segments at each and every joint articulation in the fingers of the hands.

2. The device of claim 1 wherein said measurement and input means includes means for a therapist to select an anotomic locus for measurement with has hands and enter data corresponding to the dimension with some body part other than his hands, thereby leaving his hands free to move rapidly from one dimension to another during the course of the evaluation.

3. The device of claim 1 wherein the measuring and input means includes a pointer or manual stylus assembly for a therapist or other expert human to bring into physical contact with a pre-determined anatomic locus on the hand, and means for the therapist to actuate the measuring and input means and thereby cause a measurement to be taken.

4. The device of claim 1 wherein the disability determining means includes means to calculate maximum and minimum angles of flexion and extension of the fingers and thereby determine the range of motion possible.

5. The device of claim 1 further comprising means for the therapist to enter data into the computer means corresponding to the measurement of other physiological parameters of the hand.

6. The device of claim 5 further comprising a dynamometer, a pinch gauge, and means interconnecting same to the computer means so that data generated by same is directly entered into the, computer means.

7. A device to perform the clinical evaluation of the range of motion of a patient's hands, said device comprising a computer means, a pointer means, a reference, means directly connected to the computer means to generate data corresponding to the position of the pointer means in three dimensional space with respect to the reference, and means for a therapist to cause data generated by the position means to be stored in the computer means so that a therapist can enter data into the computer means corresponding to the maximum flexion and extension of the patient's hands, said computer means having means to calculate and communicate the range of motion.

8. The device of claim 7 further comprising means for a therapist to enter data into the computer means corresponding to the measured sensitivity of the patient's hands, the computer means having means to calculate and communicate the degree of disability of the patient's hands.

9. The device of claim 8 further comprising means to generate data corresponding to the gripping strength of the patient's hands, and means to communicate said data to the computer means.

10. The device of claim 8 further comprising means to generate data corresponding to the pinch strength of the patient's hands, and means to communicate said data to the computer means.

11. The device of claim 7 further comprising a work station for containing said device, the work station having a working surface on which the patient's hands are placed for the clinical evaluation, the reference being mounted substantially adjacent to the working surface, and the work station having a shield to minimize electromagnetic interference.

12. The device of claim 7 further comprising means to measure the range of motion of the wrist from measurements taken at the radius and ulna as the wrist is moved from a neutral position to each of a maximum supination position and a maximum pronation position.

13. A clinical range of motion and disability evaluation device comprising a work station having a work surface, a personal computer, a three-dimensional six degree of freedom position locator and wand directly connected to the personal computer, said three-dimensional position locator including a common reference mounted to the work station substantially adjacent the working surface and having means to generate data corresponding to the position of the wand with respect to said reference, a second means connected to the personal computer to control the entry of data from the three-dimensional position locator to the computer wherein a therapist may selectively orient the wand at a plurality of points across a patient's hand and input data corresponding to the position of the joints while the hand is in a state of maximum flexion and extension, and the computer having means to calculate the angles of maximum extension and flexion and a degree of disability therefrom.

14. The device of claim 13 further comprising an electromagnetic shield mounted in the work station and spaced apart from the working surface to shield the common reference from electromagnetic interference.

15. The device of claim 13 further comprising a dynamometer and pinch gauge connected directly to the personal computer to permit data entry into the computer corresponding to the grip strength and pinch strength of a patient's hand.

* * * * *